United States Patent [19]

Castillo et al.

[11] Patent Number: 4,886,054
[45] Date of Patent: Dec. 12, 1989

[54] KNEE BRACE WITH CAMMED STOP LEVER

[75] Inventors: Edward L. Castillo; James D. Castillo, both of Mission Viejo; Michael S. Castillo, San Clemente, all of Calif.

[73] Assignee: Innovation Sports, Inc., Irvine, Calif.

[21] Appl. No.: 262,609

[22] Filed: Oct. 26, 1988

Related U.S. Application Data

[62] Division of Ser. No. 68,030, Jun. 29, 1987.

[51] Int. Cl.⁴ ............................................. A61F 5/04
[52] U.S. Cl. .................................... 128/80 F; 128/80 C
[58] Field of Search ................ 623/39; 128/80 C, 88, 128/80 F

[56] References Cited

U.S. PATENT DOCUMENTS

| | | | |
|---|---|---|---|
| D. 269,379 | 6/1983 | Bledsoe | D24/64 |
| 1,390,915 | 9/1921 | Loth . | |
| 2,883,982 | 4/1959 | Rainey | 128/80 C |
| 3,030,634 | 4/1962 | Bair | 623/39 |
| 3,779,654 | 12/1973 | Horne | 403/62 |
| 3,785,372 | 1/1974 | Craig | 128/30 C |
| 3,817,244 | 6/1974 | Taylor | 128/80 C |
| 3,902,482 | 9/1975 | Taylor | 128/80 F |
| 3,958,569 | 5/1976 | Vosburgh | 128/80 C |
| 4,241,730 | 12/1980 | Helfet | 128/80 C |
| 4,361,142 | 11/1982 | Lewis et al. | 128/80 C |
| 4,407,276 | 10/1983 | Bledsoe | 128/80 C |
| 4,428,369 | 1/1984 | Peckham et al. | 128/80 C |
| 4,493,316 | 1/1985 | Reed et al. | 128/80 C |
| 4,523,585 | 6/1985 | Lamb et al. | 128/80 C |
| 4,554,913 | 11/1985 | Womack et al. | 128/80 C |
| 4,599,998 | 7/1986 | Castillo | 128/77 |
| 4,603,690 | 8/1986 | Skeen | 128/80 C |
| 4,628,916 | 12/1986 | Lerman et al. | 128/80 C |
| 4,665,905 | 5/1987 | Brown | 128/80 C |
| 4,691,097 | 7/1987 | Pansiera | 128/77 |
| 4,699,129 | 10/1987 | Aaserude et al. | 128/80 C |
| 4,723,539 | 2/1988 | Townsend | 128/80 C |

FOREIGN PATENT DOCUMENTS

1491569 6/1969 Fed. Rep. of Germany .
2432766 4/1975 Fed. Rep. of Germany .

Primary Examiner—William Pieprz
Assistant Examiner—Tonya Lamb
Attorney, Agent, or Firm—Stetina and Brunda

[57] ABSTRACT

A brace for supporting a joint formed of a plurality of joint members is disclosed. The brace includes first and second frame members disposed on opposite sides of the joint to be supported, and first and second hinge members disposed substantially adjacent the joint and connected to the frame members to pivot the frame members about the joint. The frame members may be formed of separable portions engageable with each other at variable locations along the length thereof. Adjustment of the engagement location being effective to vary the orientation of at least one of the frame member portions with respect to at least one of the hinges. The brace is therefore adjustable to conform to lateral curvature of the joint members. The hinge members may be formed to regulate rotation of at least one of the frame members about the joint to provide close support to the joint members during unlocking of the joint. Such close support is provided by separately pivoting the frame members about the hinge member such that the relative rotational movement of the frame members varies in accordance with the relative movement of the joint members supported by the brace.

5 Claims, 4 Drawing Sheets

KNEE BRACE WITH CAMMED STOP LEVER

The subject application is a divisional application of U.S. Ser. No. 068,030, filed on June 29, 1987, entitled KNEE BRACE HAVING ADJUSTABLE WIDTH FRAME PIVOTED TO CUFFS (AS AMENDED).

FIELD OF THE INVENTION

The present invention relates to braces for supporting bone joints, and, more particularly, to a knee brace adjustable to compensate for imbalances between medial and lateral support of the knee as well as curvatures at the level of the knee.

BACKGROUND OF THE INVENTION

The knee joint is generally considered the largest and most complicated joint in the body. Though frequently considered a hinge joint the knee is actually two joints, lateral and medial, between femur and tibia, and one arthrodial joint between the patella and the femur. The chief movements of the knee are flexion and extension.

The flexion and extension movements of the knee joint are not simply pivotal movements about a fixed axis. During flexion, the axis around which movement takes place shifts backward, and during extension it shifts forward. This is different from a more typical hinge joint, such as an elbow, where the axis of rotation does not shift. As full extension is reached the femur is rotated inward and the joint is "locked" with the ligaments taut. The joint is, in effect, disposed in a locked position with the ligaments taut. This gives the joint greater stability in the extended position. As flexion is initiated, the femur initially lowers or moves downwardly with a small external rotation of the femur which unlocks the joint and subsequently the femur rotates or rolls about the joint to full flexion. Accordingly, the initial unlocking of the knee joint during flexion precedes actual full rotation of the knee.

A simple hinge brace generally fails to provide proper support to limit permissible rotation during the unlocking motion. For a brace to more fully support the knee joint and facilitate rehabilitation of an injured joint the brace should more closely analogize the movement of the knee than a simple hinge does. Ideally, a brace will simulate the movement of the knee joint to provide greater support and stability through the range of flexion and extension of the knee joint.

Contemporary braces generally fail to provide such precise simulation of the knee joint as described in connection with the present invention. Consequently, those devices generally provide inadequate support and possibly permit reinjury of the knee joint, even when the brace is worn. Most contemporary braces are further deficient in that the vertical plane of the brace is fixed at the time the brace is manufactured and may be unsuitable for individuals having different curvatures at the level at the knee. Such curvatures are commonly attributable to an imbalance between the medial and lateral support of the knee. Lack of adequate lateral support of the knee may produce a bowlegged condition, i.e. outward curvature at the level of the knee. A lack of medial support of the knee may produce a knock-kneed condition, characterized by an inward curvature at the level of the knee. A brace designed for individuals having normal curvature of the leg at the level the knee may therefore be uncomfortable or entirely unsuitable for bowlegged or knock-kneed persons. In recognizing this deficiency, most state of the art knee braces are manufactured on a prescription, one of a kind basis, to properly accomodate the differing physical parameters of the user. As will be recognized, such unique, one of a kind fabrication significantly increases overall cost of the knee brace as well as increases delivery time of brace to the user. Consequently, there exists a need for a brace that may be manufactured to accomodate all patients and be subsequently adjusted at the time of initial placement upon the user to support the knee joints of users having various degrees of leg curvature at the level of the knee.

In addition to the adjustability and operational deficiencies generally associated in the prior art, most prior art knee braces additionally do not permit the effective use of the knee brace in both post surgical as well as rehabilitation applications. As will be recognized, in post surgical applications, i.e. that period of time of approximately two to six weeks following reconstructive knee surgery, there is a substantial need to provide extremely firm support for the knee joint and limit hyperextension and hyperflexion of the knee. Subsequently, during rehabilitation periods it is desirable to gradually reduce the support applied to the knee by the brace to facilitate strengthening of the knee muscles and additionally allow greater extension and flexion of the knee joint. Unfortunately, the current state of the art of knee braces has not adequately addressed the application of knee braces to both post surgical and/or rehabilitation applications and hence, there exists a substantial need in the art for an improved knee brace which is specifically designed and adapted to accomodate the differing considerations encountered in post surgical and rehabilitation applications.

As described below the present invention is directed to an improved brace which more closely simulates the movements of the joint to provide enhanced support of the joint. The invention is further directed to a brace that is adjustable to accommodate curvatures of the joint members at the level of the joint. These and other objects and advantages of the invention will be described below in connection with the appended drawings illustrating the presently preferred embodiments of the invention.

SUMMARY OF THE INVENTION

A brace for supporting a joint formed of a plurality of joint members is disclosed. The brace includes first and second frame members disposed on opposite sides of the joint to be supported, and first and second hinge members disposed substantially adjacent the joint and connected to the frame members to pivot the frame members about the joint. The frame members may be formed of separable portions engageable with each other at variable locations along the length thereof. Adjustment of the engagement location being effective to vary the orientation of at least one of the frame member portions with respect to at least one of the hinges. The brace is therefore readily adjustable to conform to lateral curvature of the joint members. The hinge members may be formed to regulate rotation of at least one of the frame members about the joint to provide close support to the joint members during unlocking of the joint. Such close support is provided by separately pivoting the frame members about the hinge member such that the relative rotational movement of the frame members varies in accordance with the relative movement of the joint members supported by the brace.

In the presently preferred embodiment the frame members are formed as first and second generally J-shaped members having vertical portions connectable to the hinges and horizontal portions engageable with each other at variable locations along the length thereof. The horizontal portions are secured in place with respect to each other by a turret rotatably mounted to a support cuff. Support cuffs having different widths may be utilized consistent with the stage of rehabilitation of the user, thereby allowing the brace to be effectively utilized in both post surgical and rehabilitation applications. Varying the engagement location between J-shaped portions of the frame members permits the frame members to be manufactured in standardized configurations and subsequently be adjusted upon initial fitting to a user to conform to the various lateral curvatures of the joint, such as conditions commonly referred to as bowleggedness and knock-knees.

The hinge members are preferably formed such that the frame members rotate about separate pivot locations, and are pivotally connected to each other, such that one of the frame members has little rotation as the first frame member is moved from the extension position. However, as the first frame member continues to move the relative rotation of the second frame member increases to approximately that of the first frame member. Such limitation in the initial rotational movement of the second frame member permits the brace to closely support the joint members during unlocking of the joint. The hinge members are further provided with a lever arm which translates in response to rotation of the frame members. The translation of the lever arm may be regulated by adjustable stops such that the frame members may be variably limited with respect to extension or flexion movement as desired.

The brace may also be provided with support members extending between portions of the frame members to secure the frame members in place with respect to the leg of the user. In the rehabilitation embodiment of the present invention wherein a narrower cuff is utilized, the support members are formed as molded plastic members shaped to generally conform with front portions of the user's leg.

DETAILED DESCRIPTION OF THE PREFERRED EMBODIMENTS

The description set forth below in connection with the appended drawings is intended merely as a description of the presently preferred embodiment of the invention, and is not intended to represent the only form in which the present invention may be utilized. The description sets forth the functions and structural elements of the invention in connection with the illustrated embodiment. It is to be understood, however, that the same, or equivalent functions and advantages of the invention may be accomplished by different embodiments that are also intended to be encompassed within the spirit and scope of the invention.

Figures 1, 2, 3, 4, 5, 6:
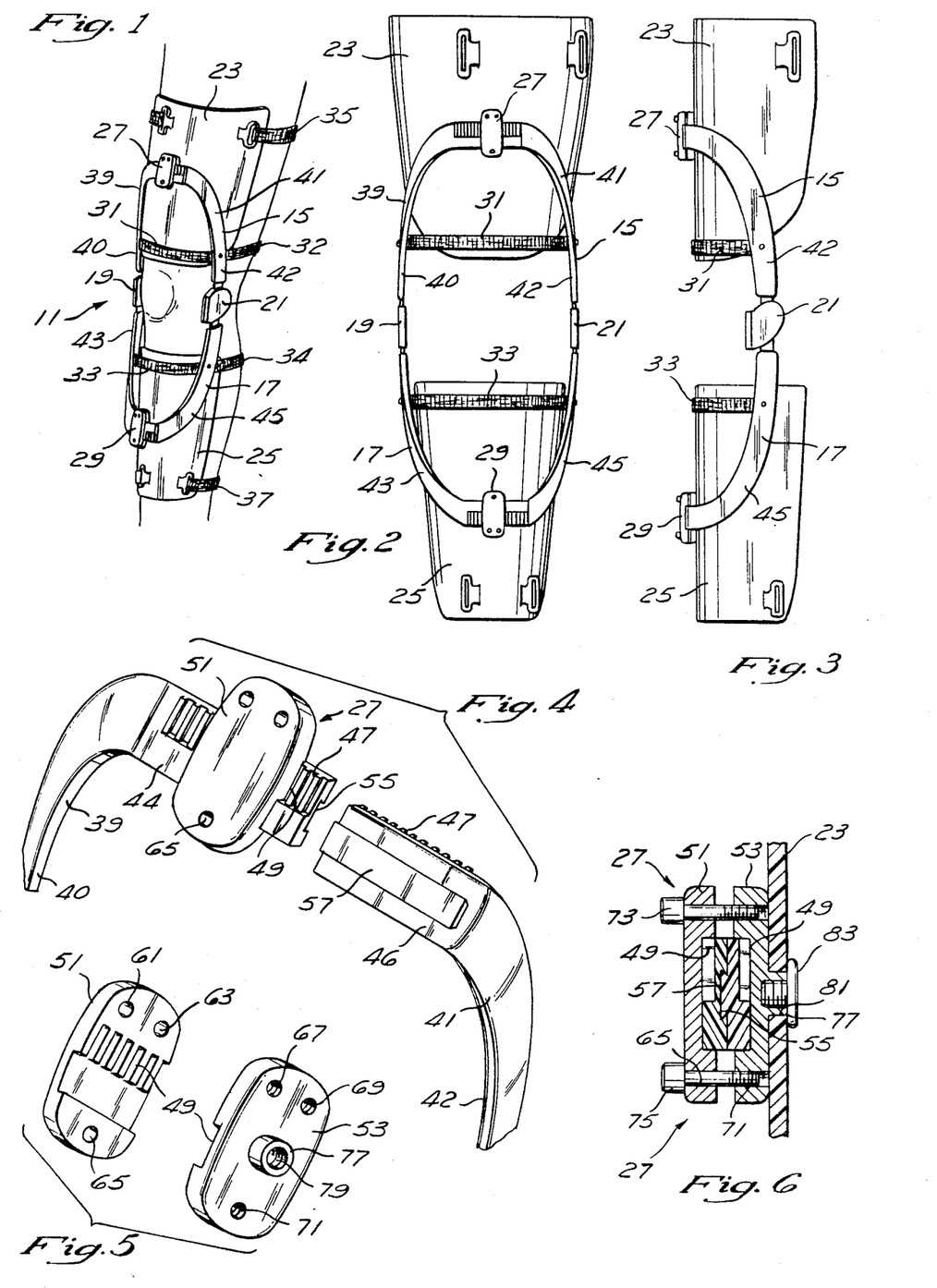
FIG. 1 is a perspective view of the presently preferred embodiment of the invention depicted in a post surgical configuration, fitted to the leg of a user.
FIG. 2 is a front view of the invention illustrated at FIG. 1.
FIG. 3 is a side view of the invention illustrated at FIG. 1.
FIG. 4 is an enlarged perspective view of a portion of the frame members, shown disconnected.
FIG. 5 is an enlarged perspective view of the turret for joining portions of the frame members.
FIG. 6 is a cross-sectional view of the turret shown in FIG. 1, taken along line 6—6.
Figure 7:
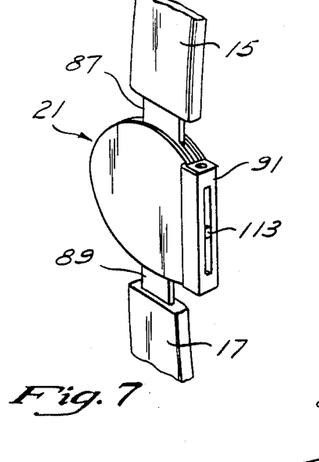
FIG. 7 is an enlarged perspective view of the hinge connected to portions of the frame members.

FIG. 1 illustrates the presently preferred embodiment of the invention 11 depicted in its post-surgical configuration as worn on the leg of the user. In such a post-surgical application it is desired that the brace provides maximum reliable support to the joint and limit flexion and extension of the knee joint to enable rapid healing of the knee joint and leg muscles typically effected during reconstructive knee surgery. The embodiment set forth at FIG. 1 is intended to support the knee joint and is secured to the user's leg about the thigh and calf. It is anticipated, however, that in its broader aspects the invention may be utilized to support other joint members in the same or similar manner to that illustrated in connection with the presently preferred embodiment. Accordingly, it is to be understood that the particular shape arrangement and interconnection of the parts set forth in connection with the appended figures may be modified consistent with the particular joint to be supported, without departing from the broader aspects of the invention.

As illustrated at FIG. 1, the invention 11 comprises generally U-shaped frame members 15 and 17 disposed in opposing orientation about the knee of the user, and connected at hinges 21. The frame members 15 and 17 each comprise two, substantially J-shaped portions as described more fully below. The frame members 15 and 17 are connected to semi-rigid cuffs 23 and 25 by connecting turrets i.e. rotating attachments or clamping members 27 and 29, respectively. Turrets 27 and 29 are formed to facilitate lateral rotation of the U-shaped frame members about the cuffs, as described more fully below. Adjustment mount straps 31 and 33 extend across the width of frame members 15 and 17, respectively, and releasably engage straps 32 and 34 respectively which secure the frame in place with respect to the leg of the user. Straps 35 and 37 further secure cuffs 23 and 24, respectively, in place and extend about the leg of the user. Preferably the straps 32, 34, 35 and 37 are adjustable in length to properly secure the brace device to the leg of a user and include quick connect and disconnect end fasteners which enable the brace to be rapidly attached to and removed from the leg of a user. Further, the straps 32, 34, 35 and 37 are removably attached to the strap mounts 31 and 33 and cuffs 23 and 25 so as to accomodate replacement of the cuffs 23 and 25 with substitute cuffs utilized in rehabilitation applications as will be described in more detail below.

FIG. 2 illustrates a front view of the invention 11 set forth at FIG. 1, with cuff straps 32, 34, 35 and 37 detached. FIG. 3 is a side view of the invention illustrated at FIG. 2. As shown at FIGS. 2 and 3 the frame members 15 and 17 are formed to curve laterally and medially to accommodate the leg shape of the user. The frame members 15 and 17 extend upward and flare forward to conform to the bone and muscle structure of the user's leg. The width of the frame members is adjustable, as described below, to conform to the tuberosity of the user's leg and to vary the angular orientation of the frame members with respect to the hinges 19 and 21. Such variability allows a single brace to be used to support joints where the size and curvature of the joint members may vary.

The U-shaped members 15 and 17 are formed of a plurality of variably connected portions so as to permit adjustability of the dimensions and orientation of the frame members. Frame member 15 is formed to include frame portions 39 and 41, joined at turret 27. U-shaped frame member 17 includes portions 43 and 45, joined at turret 29. Though the configuration of each of the portions 39, 41, 43 and 45 generally varies somewhat between portions in the presently preferred embodiment, each of the portions 39, 41, 43 and 45 is formed as a generally J-shaped member having a vertical portion, e.g. vertical portions 40, 42, extending from the hinge 21, curving to form a generally horizontal portion, e.g. horizontal portions 44, 46, extending to or beyond the turrets 27 or 29. The overlap of the substantially J-shaped portions 39 and 41, and 43 and 45 may be varied so as to adjust the width of the frame member and the orientation of at least one of the vertical portions with respect to the hinges 19 and 21. Strap mounts 31 and 33 extend across the width of U-shaped members 15 and 17, respectively and abut against and connect to portions of cuffs 23 and 25, respectively. The straps 32 and 34 may therefore urge cuffs 23 and 25 to remain in place against the front surface of the leg of the user.

FIGS. 4, 5 and 6 illustrate the means for connecting the substantially J-shaped members to form the U-shaped frame member. As shown at FIG. 4 portions 39 and 41 of frame member 15 may be separated from each other and from turret 27. One or both of the J-shaped members, such as member 39, is provided with a partially ridged or grooved surface 47 that is mateable to the ridged or grooved surface 49 formed on the front and/or rear portions 51 and 53 respectively of turret 27. Portion 39 may further be provided with a dove tail recess 55 formed on the back surface of member 39. The recess 55 is sized to receive a complimentary shaped elongate member 57 formed on the front surface of member 41. Member 57 slidably engages recess 55 so as to vary the width of U-shaped frame member 15 and the orientation of the vertical portions 40, 42 with respect to the hinges. When members 35 and 41 are engaged to the desired length along recess 55 and member 57, the turret 27 is secured together to hold members 39 and 41 in place in that orientation, and to the cuff 23.

As shown at FIG. 5 turret 27 includes front portion 51 and back portion 53. As previously indicated grooved surfaces 49 are formed on the portions 51 and 53 to engage surfaces 47 formed on members 39 and 41. Apertures 61, 63, 65, 67, 69 and 71 are formed to receive fasteners such as screws 73 and 75 to secure J-shaped portions 39 and 41 firmly in place with respect to each other and with respect to the turret front and back portions 51 and 53.

As shown at FIGS. 5 and 6 turret 27 is provided with collar 77 having an aperture 79 formed therein. Collar 77 is formed to fit within aperture 81 formed in the cuff 23. Fastener 83 is formed to extend through aperture 81 and engage turret 27 within aperture 79. Fastener 83, cuff 23 and turret 27 cooperate to permit lateral rotation of the turret 27 with respect to the cuff 23 about the axis of fastener 83.

It is to be understood that an alternate turret constructions, including other means of varying the width and orientation of the frame member 15, may be implemented without departing from the broader aspects of the invention. Similarly, it is anticipated that alternate means of rotatably securing the frame member to the support cuff may also be implemented other than that specifically set forth herein.

As shown, the frame members 15 and 17 are pivotally attached to one another by way of a pair of hinge elements 21 which are formed having identical structure and operation. In the preferred embodiment, regulation of the relative movement of the frame members 15 and 17 permits one joint member to initially rotate about the joint more rapidly than the other joint member, and thereby simulates unlocking and locking of the knee joint. Each hinge 21 is constructed such that one joint member, i.e. the femur, can rotate relatively freely about a pivot while the rotation of the second joint member, i.e. the tibia, is adjusted and the joint is "unlocked". After rotation of first joint member beyond a certain point the second joint member may then rotate more freely, i.e. as freely as the first joint member. Such regulation of the relative movement of the frame members simulates the normal bone and muscle movements of the knee joint to provide support and resistance consistent with the natural movement of the joint members.

Figure 8:
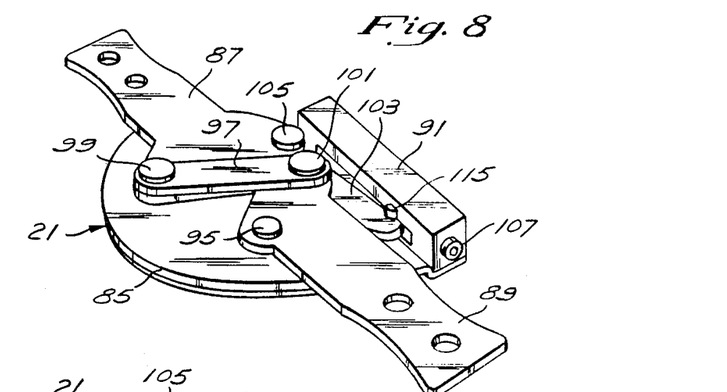
FIGS. 8 and 9 are perspective views of the hinge illustrated at FIG. 7, partially disassembled to illustrate movement of the hinge.
Figure 9:
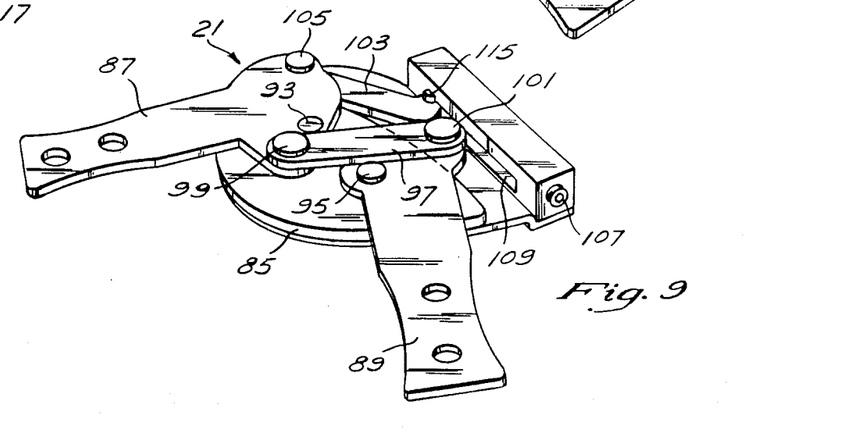

FIGS. 8 and 9 are perspective views of the hinge 21, partially disassembled, to illustrate the movement of the connecting members 87 and 89, which are connectable to the frame members 15 and 17, respectively. As shown therein hinge 21 comprises a base plate 85 having a second plate 86 stacked or juxtapositioned thereon. The second plate 86 is somewhat smaller than base plate 85. A portion of the periphery of the second plate 86 forms a camming edge 111 which extends across the mid-region of base plate 85.

Hinge legs or members 87 and 89 are pivotally affixed to the upper surface of second plate 86 by way of pivot members 93 and 95. An elongate linking member 97 is pivotally attached to the bodies of hinge members 87 and 89 by way of pivot members 99 and 101, respectively. Thus, hinge members 87 and 89 are linked together so that they will undergo concomitant, related pivotal movement.

A stopping lever 103 is secured to hinge member 87 by way of pivot member 105. Stop lever 103 is juxtapositioned to the upper surface of base plate 85 proximate to the camming edge 111 of second plate member 86.

The distal end of stop lever 103 is inserted into groove 109 of guide member or block 91. A small projection 115 is formed on the upper side of stop lever 103 and rides against the edge of guide member 91 when the distal end of stop lever 103 is fully inserted into guide track 109. When hinge member 87 undergoes pivotal movement, the distal end of stop lever 103 will correspondingly ride within groove 109. Stop lever 103 is provided with a camming edge 104 adjacent the camming edge 111 of second plate member 86. Camming surface 104 of stop lever 103 will cam against the camming surface 111 of second plate member 86 to continually urge the stop lever 103 in the direction of groove 109 thereby preventing escape of the distal end of stop lever 103 from its position within groove 109.

As described more fully below in conjunction with FIGS. 10, 11, and 12, stop lever adjusting screws 107 and 109 may be independently advanced or retracted from the opposite ends of groove 109. Thus, the adjusting screws 107 and 109 may be adjusted to provide different end stops or end points within groove 109. Such will limit and regulate the extent of linear movement of stopping lever 103 and, consequently, limit the extent of rotation of hinge connecting members 87 and 89.

FIGS. 7-12 illustrate the structure and operation of the hinges 19 and 21 disclosed more generally at FIGS. 1, 2 and 3. As described more fully below hinge 21 is connectable to frame members 15 and 17 to facilitate rotation of the frame members about the hinge 21. The hinge is further constructed to regulate movement of the frame members to limit extension and flexion of the joint for either post-surgical or gradual rehabilitation of the knee and to simulate locking and unlocking of the joint members. Regulation with respect to the extent of movement permits the invention to be utilized by patients during various stages of rehabilitation. For example, the hinge may be configured to provide limited rotational movement of the femur and tibia about the knee joint for post-surgical applications, thereby limiting extension and flexion of the knee joint. The hinge may later be adjusted to permit greater movement for rehabilitation applications as the injury heals, although in all instances hyperextension and hyperflexion of the joint is eliminated.

The connecting members 87 and 89 are themselves connected together by a rigid linking member 97 secured to and extending between pivot 99 and pivot 101. The location of pivots 99 and 101 with respect to pivots 93 and 95 is such that rotational movement of connecting member 87 about pivot 93 initially causes little rotation of connecting member 89 about pivot 95. However, as connecting member 87 continues to rotate about pivot 93 the linking member 97 causes greater relative rotation of connecting member 89 about pivot 95. The change in relative rotation of connecting members 87 and 89 may be mechanically explained in that initial movement of connecting member 87 is largely translated to rotation of linking arm 97 about pivot 101. However, as connecting member 87 continues to rotate about pivot 93 less of the movement of linking member 97 is accommodated by rotation about pivot 101 and therefore connecting member 89 is urged to rotate about pivot 95 at substantially the same rotational rate that connecting member 87 rotates about pivot 93.

It is to be understood that by adjusting the construction of the linking member 97, the connections between the linking member 97 and connecting members 87, 89, and the location of the linking member pivots, 99, 101 with respect to the connecting member pivots 93, 95, a variety of different motion patterns may be implemented to simulate the motion of different joints. Consequently different embodiments of the invention may be implemented to simulate the movement of joints other than that set forth in connection with the illustrated embodiments.

Figures 10, 11, 12:
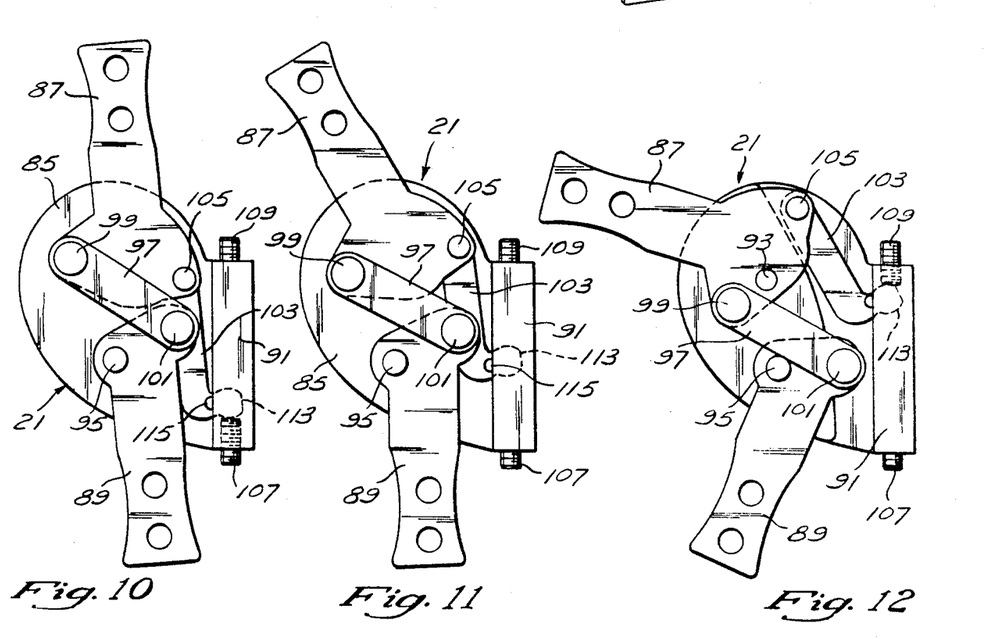
FIGS. 10, 11 and 12 are enlarged side views of the hinge shown at FIG. 7, partially disassembled to further illustrate movement of the hinge.

FIGS. 10, 11 and 12 are side views of the hinge 21 illustrating the manner in which the rotational movement of the connecting members 87 and 89 may be regulated to limit flexion and extension of the joint. As described above stop lever 103 is pivotally connected to connecting member 87 at pivot 105 and extends into stop lever guide member 91. Portion 113 of stop lever 103 extends into the guide member 91 and moves along the length of the guide member 91 in response to rotation of connecting member 87. Protrusion 115 limits the extent that the stop lever extends into guide member 91 and facilitates translation of portion 113 within the guide member 91.

As illustrated at FIGS. 10, 11 and 12 the translation of portion 113 within guide member 91 is regulated by the extension of stop lever adjusting screws 107 and 109. As screw 107 is further adjusted into guide member 91 the extension of the joint members is limited by a corresponding amount. As stop lever adjusting screw 109 is further adjusted into guide member 91 the flexation of the joint members about the joint is further limited. As will be apparent to those skilled in the art, a proper adjustment of stop lever adjustment screws 107 and 109 will allow the invention to be utilized to facilitate rehabilitation of injuries over periods of time. As the joint rehabilitates the safe levels of extension and flexation may be increased.

With the structure defined, the operation of the present invention and its advantages in its post-surgical configuration may be described. In the post-surgical configuration, an orthopedic medical practitioner may position the composite brace 11 upon upon the leg of a user following knee surgery, with the straps 32, 34, 35 and 37 being manually adjusted to retain the brace tightly upon the leg of a user at a desired location. The threaded fasteners 73 and 75 of the turrets 27 and 29 may then be loosened to allow the practitioner to adjust the width, i.e. lateral spacing between the upper and lower frame members 15 and 17 to obtain proper positioning of the hinges 21 relative to the knee joint and compensate for any bowleggedness or knock-knee conditions of the user. As will be recognized, any variation in the plane of the upper and lower portions of the joint is accomodated by pivoting or swivel movement of the turrets about their central access or pin 83 relative the cuffs 23 and 25. Subsequently the fasteners 73 and 75 may be manually tightened causing the turrets 27 and 29 to rigidly lock the adjusted orientation of the frame members relative the cuffs and leg of a user. Subsequently, the screws 107 and 109 of each hinge 21 may be adjusted to limit the extension and flexure of the knee joint to within desired ranges to thereby eliminate any hyperextension or hyperflexion of the joint during post-surgical use. The straps 32, 34, 35 and 37 may then be readjusted in length to properly maintain the composite brace upon the user's leg. As such, it will be recognized by use of the various adjustment mechanisms of the present invention, a standarized construction of the knee brace permits adjustment after manufacture to accomodate the particular physical parameters of the individual. Once the brace is positioned upon the knee, the use of quick disconnect and connect fastener ends on the strap members 32, 34, 35 and 37 allow the composite brace to be rapidly attached to and removed from the leg of user without any additional adjustment.

It is an important feature of the present invention that the brace device is specifically designed to permit its use in both post surgical as well as rehabilitation applications. The modification of the structure of the present invention for such a rehabilitation application is depicted in FIGS. 13–16. As will be recognized, in rehabilitation therapy applications it is desired that the weight of the composite brace device be maintained at a minimum to permit comfort during use, as well as permit the joint to be flexed and extended through a greater distance to rebuild the muscle structure weakened through previous surgery or injury to the user.

Figure 13:
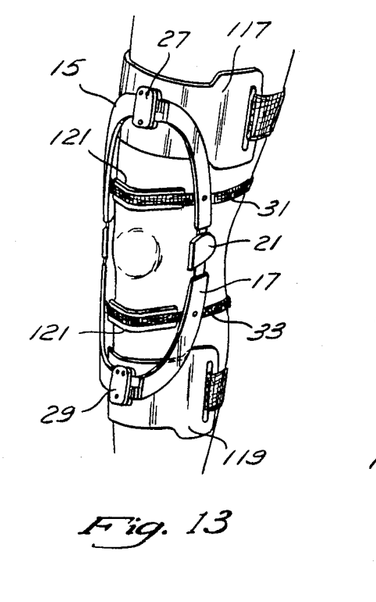
FIG. 13 is a perspective view of the preferred embodiment of the invention depicted in a rehabilitation configuration incorporating a different cuff and support strap arrangement.
Figure 14:
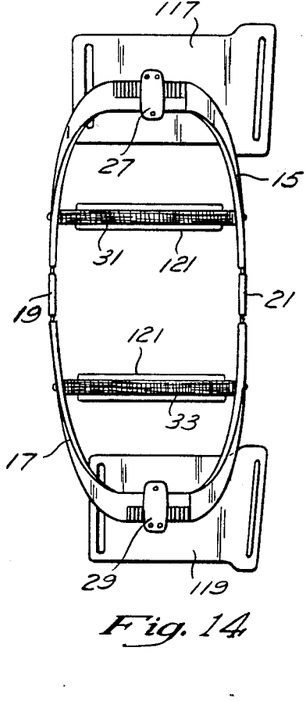
FIG. 14 is a front view of the embodiment illustrated at FIG. 13.
Figure 15:
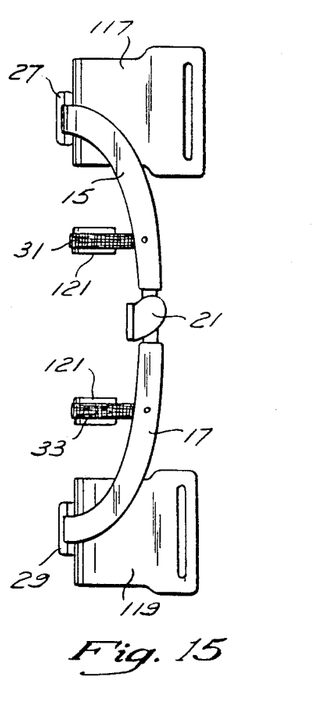
FIG. 15 is a side view of the embodiment illustrated at FIG. 13.
Figure 16:
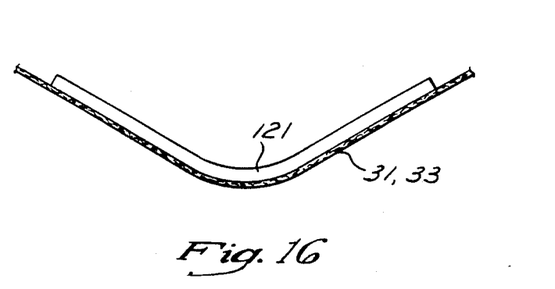
FIG. 16 is a top view of the support cuff and strap shown at FIGS. 13-15.

Referring to FIGS. 13, 14 and 15, the detailed construction of the knee brace of the present invention depicting its modification to a rehabilitation structure is shown. As will be recognized, in this rehabilitation embodiment the structure is identical to that shown in relation to the post-surgical environment previously described. However, the semi-rigid cuffs 23 and 25 are replaced with smaller, lighter, flexible pads or cuff pads 117 and 119 which are connected to a respective turret 27 and 29 in a manner previously described. In addition, the strap mounts 31 and 33 do not attach to the cuffs 117 and 119 but rather, mount a generally V-shaped saddle member 121. As illustrated in FIG. 16, the saddle member 121 may be implemented as a semi-rigid member sized to generally conform to the tubrosity of the leg of a user. The compression force applied through the strap members 32 and 34 to the saddles 121 serve to distribute the pressure caused by the strap across the surface of the leg and avoid irritation associated with the use of elastic materials that expand and contract along the surface of a leg.

As will be recognized, the modification of the present invention from the post-surgical structure to its rehabilitation structure can be easily accomodated merely by removal of the central pin or access 83 of each of the turrets 27 and 29 and removal of the semi-rigid cuff members 23 and 25 therefrom and the substitution and mounting of the flexible cuff pads 117 and 119 thereto. Similarly, the straps 32, 34, 35 and 37 may be removed from the post-surgical cuffs 23 and 25 and attached to the pads 117 and 119 in an analogous manner. Subsequently, the entire brace structure may be rapidly mounted upon the leg of the user to provide significant support to the user's knee joint yet permit more unrestricted use of the muscles associated with the knee joint. Further, the adjustable screw stops of the hinge may be adjusted to allow greater extension and flexion of the joint necessary for rehabilitation purposes.

Figures 17, 18:
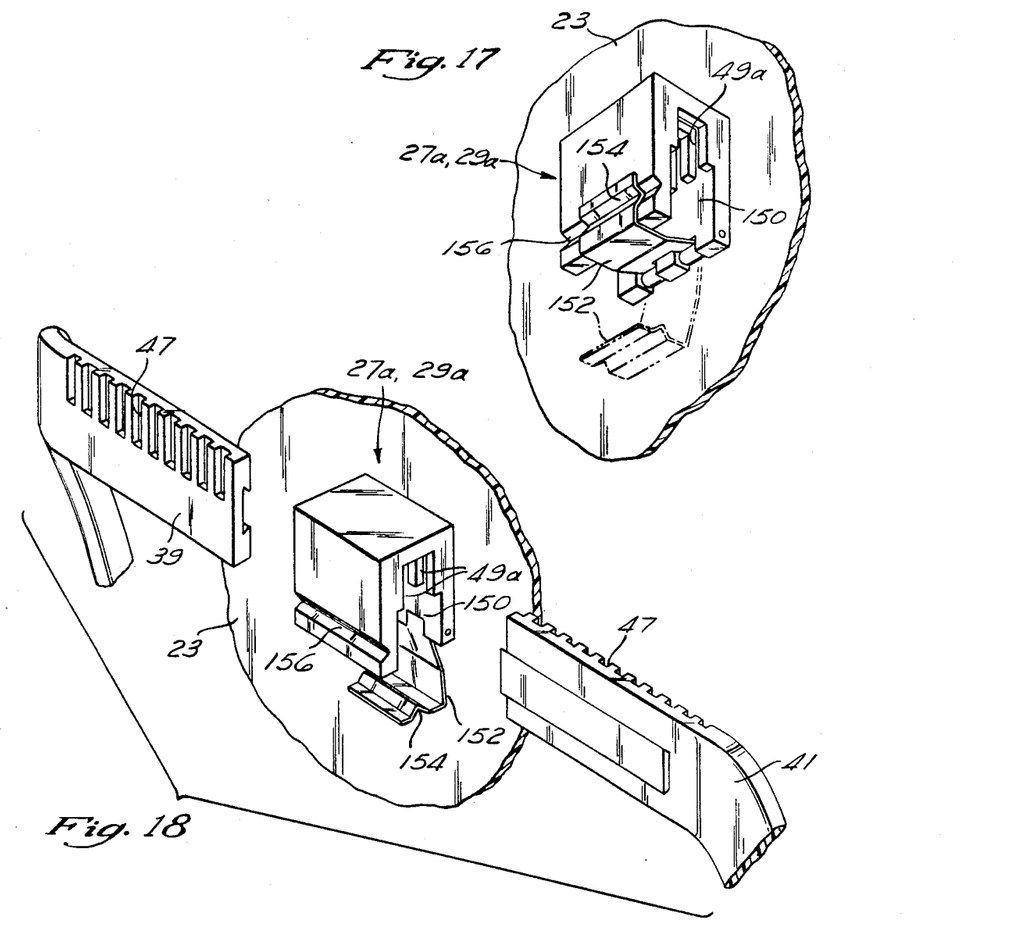
FIG. 17 is a perspective view of an additional embodiment of the turret for joining portions of the frame members.
FIG. 18 is a perspective exploded view of the additional embodiment of the turret of the present invention.
Figure 19:
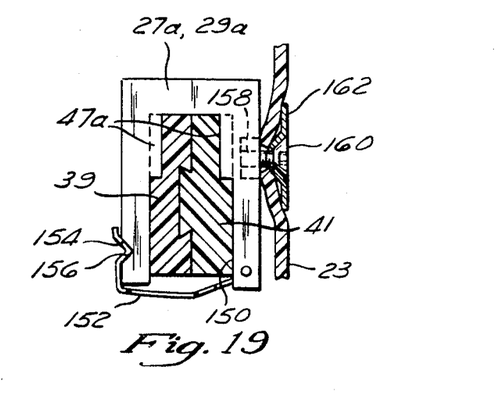
FIG. 19 is a crossectional view illustrating the assembly of the additional embodiment of the turret with the portions of the frame members.

Referring to FIGS. 17 through 19, an additional embodiment of the turrets 27a, 29a is depicted which may be used in both the post-surgical and rehabilitation configurations of the present invention. In this additional embodiment, the turrets 27a, 27b are formed in a generally U-shaped configuration defining a central opening 150 which includes partially ribbed or grooved surfaces 49a adjacent one end thereof. As will be recognized, the grooved surfaces 49a are engageable with the complimentary shaped grooved surfaces 47 formed on the frame portions 39 and 41 in a manner analogous to that previously described. A spring clip 152 is pivotally mounted to the turret 27a, 29a adjacent the lower end of the opening 150 which may be articulated from its open phantom line position to its closed full-line position shown in FIG. 17. The distal end of the clip 152 is provided with a V-shaped catch portion 154 which is received in a complimentary formed recess 156 formed on the exterior of the turret 27a, 29a. As will be recognized in its closed position, the spring clip 152 maintains a constant biasing force across opposite leg portions of the turret 27a, 29a to securely lock the frame members 39 and 41 in a desired position within the turret 27a, 29a. The turret 27a, 29a includes a threaded aperture 158 preferably formed as an insert at its rear surface which engages a threaded fastener 160 having a cup washer 162 to removably mount the turret 27a, 29a to the cuff 23. As will be recognized, with this additional embodiment of the turret 27a, 29a, the manipulation and mounting of the frame member portions 39 and 41 in a desired orientation may be facilitated rapidly and easily without the use of auxiliary tools.

As described above, the foregoing description represents only the presently preferred embodiments of the invention. Various modifications, additions and substitutions may be made to the invention with departing from the spirit or scope of the invention. Accordingly, the above description is not intended to exclude other equivalent constructions that incorporate the broader aspects of the invention.

What is claimed is:

1. A hinge for use in an orthopedic knee brace, said hinge comprising:

a generally flat base plate member having an inner surface and an outer surface;

a generally flat second plate member having an inner surface, an outer surface, and a camming edge;

said second plate member being affixed to said base plate member such that the inner surface of the second plate member is in substantial juxtaposition with the outer surface of said base plate member and further such that the camming edge of the second plate member resides above and extends over at least a portion of the upper surface of said base plate member;

first and second hinge members pivotally mounted upon the outer surface of said second plate member;

a guide block affixed to said base plate and having at least one guide slot formed therein, said guide slot having first and second end stops formed therein, said guide slot being opposite and in spaced relation to the camming edge of said second plate member;

at least one generally elongate stopping lever having first and second ends, the first end of said stopping lever being pivotally attached to one of said hinge members and the second end of said stopping lever being slidably disposed within the guide slot of said guide block, said stopping lever being positioned next to the camming edge of the second plate member such that, upon rotational movement of the hinge member to which said stopping lever is attached, a portion of said stopping lever will cam against the camming edge of said second plate member, thereby urging the second end of said stopping lever into said guide slot; and whereby said hinge is rotatable in a first direction to a point where the first end of said stopping lever abuts against the first end of said guide slot and alternately rotatable in a second direction to a point where the first end of said stopping lever abuts against the second end of said guide slot.

2. The hinge of claim 1 further comprising a linking member connecting the first hinge means to the second hinge means such that rotational movement of one of said hinge means will result in concommitant rotational movement of the other hinge means and further such that the limitation on range of pivotal movement resulting from the interaction of said stopping lever with the ends of said guide slot will cause a resultant limitation of the pivotal movement of both the first and second hinge members.

3. The hinge of claim 1 wherein at least one of said end stops comprises an adjustable end stop, said adjustable end stop being operative to adjust the length of travel of said stopping lever within said guide slot and further thereby operative to adjust the resultant range of pivotal movement of at least the hinge member to which said stopping lever is attached.

4. The hinge of claim 1 further comprising a raised projection formed on said stop lever proximate the second end thereof and operative to abut against the guide block so as to prevent passage of said stopping lever into said guide slot beyond said raised projection.

5. The hinge of claim 4 wherein the raised projection is configured so as to slide upon said guide as the hinge undergoes pivotal movement.

* * * * *